(12) United States Patent
Reimels et al.

(10) Patent No.: US 8,226,693 B2
(45) Date of Patent: Jul. 24, 2012

(54) BONE BRIDGE PROVIDING DYNAMIC COMPRESSION ON BONE FRACTURES

(76) Inventors: William J. Reimels, Goleta, CA (US); Bradford H. Hack, La Canada, CA (US)

( * ) Notice: Subject to any disclaimer, the term of this patent is extended or adjusted under 35 U.S.C. 154(b) by 853 days.

(21) Appl. No.: 11/539,401

(22) Filed: Oct. 6, 2006

(65) Prior Publication Data

US 2007/0293863 A1 Dec. 20, 2007

(51) Int. Cl.
*A61B 17/66* (2006.01)
(52) U.S. Cl. .................................................... 606/282
(58) Field of Classification Search ............... 606/71, 606/282–4, 70
See application file for complete search history.

(56) References Cited

U.S. PATENT DOCUMENTS

| | | | | |
|---|---|---|---|---|
| 4,493,317 A * | 1/1985 | Klaue | ........................... | 606/282 |
| 6,872,210 B2 * | 3/2005 | Hearn | ............................ | 606/71 |
| 2004/0225291 A1 * | 11/2004 | Schwammberger et al. | ... | 606/71 |
| 2005/0065516 A1 * | 3/2005 | Jahng | ............................. | 606/61 |
| 2005/0192581 A1 * | 9/2005 | Molz et al. | ...................... | 606/74 |
| 2006/0235405 A1 * | 10/2006 | Hawkes | .......................... | 606/69 |
| 2006/0264941 A1 * | 11/2006 | Lins | ................................ | 606/61 |

* cited by examiner

*Primary Examiner* — Kevin T Truong
*Assistant Examiner* — David Bates
(74) *Attorney, Agent, or Firm* — Laura Tunnell

(57) ABSTRACT

An orthopedic bone bridge, suitable for internally fixating and stabilizing fractured bones. The bone bridge includes: first and second bone plates for attachment to bone fragments by bone screws or the like on opposite sides of a bone fracture, a pair elongate parallel hollow legs on which the plates are mounted and the second plate is slidably engaged and is moveable with respect to the first plate, and an elastic cable or microcable attached to the first plate and extending down through the legs and around said second plate. The elastic cable is configured to provide a controlled tensile force between the plates when they are pulled into a longitudinally spaced apart position with the bone bridge then applying a correspondingly compressive force onto the bone fracture when the plates are secured to bone fragments on opposite sides of a bone fracture.

7 Claims, 6 Drawing Sheets

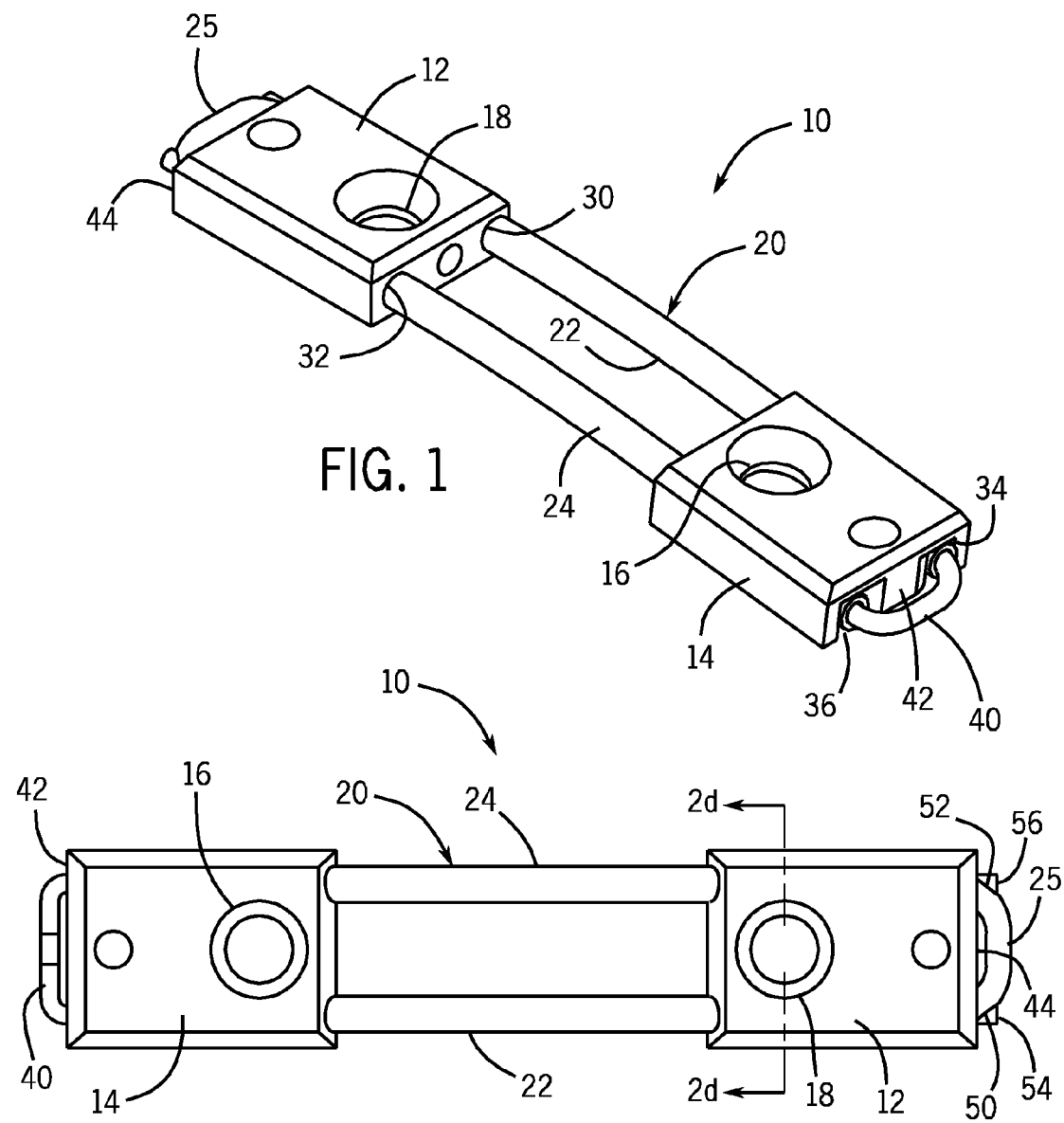
FIG. 1
FIG. 2a
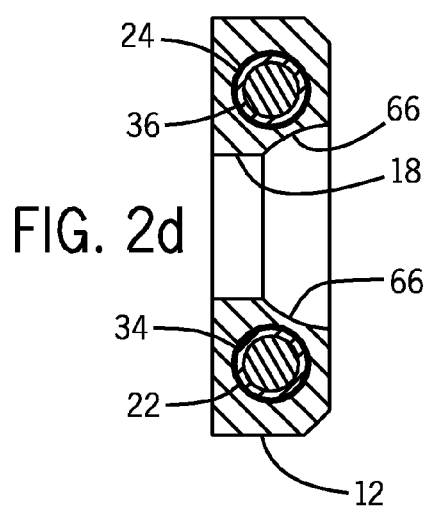
FIG. 2d

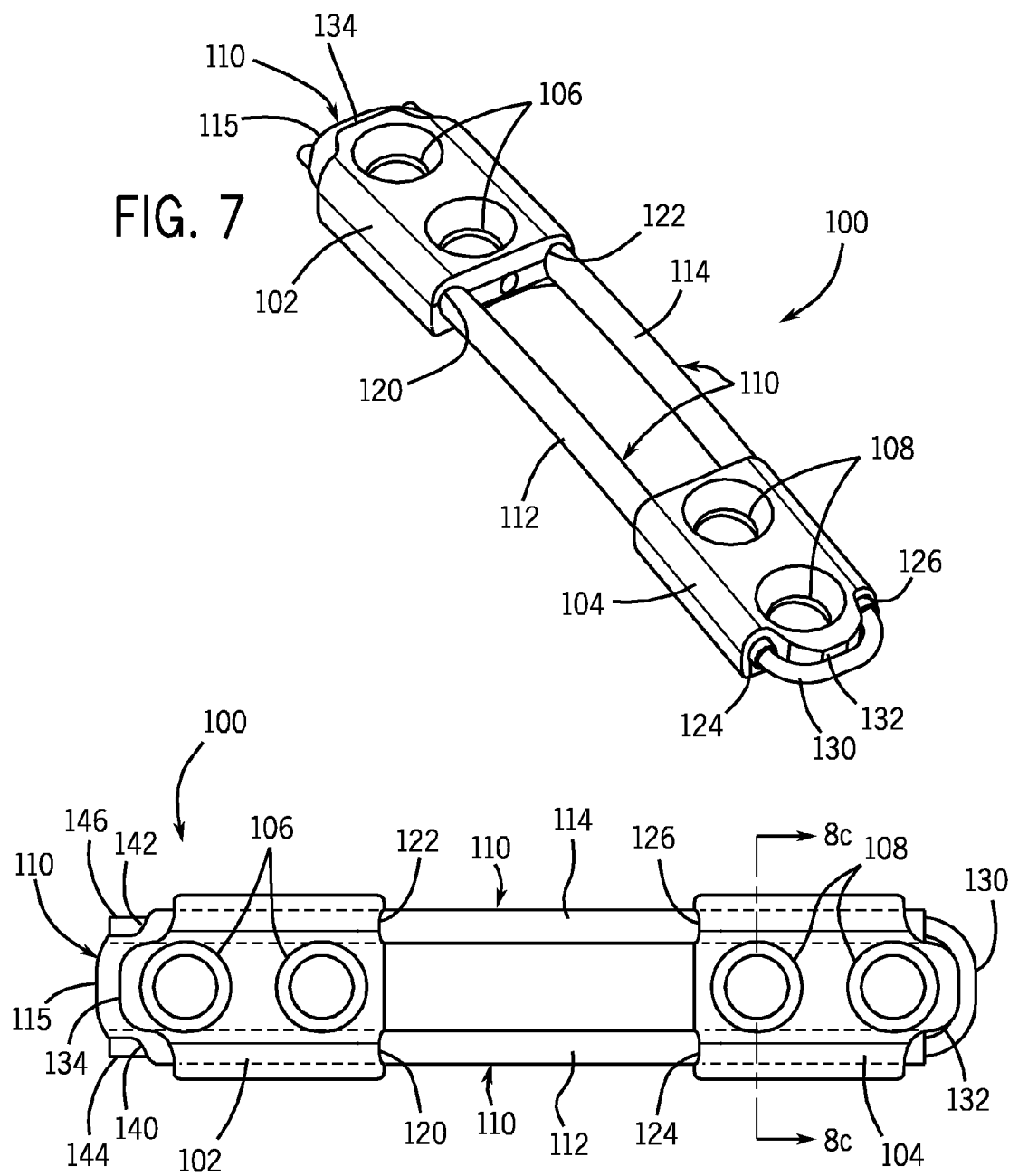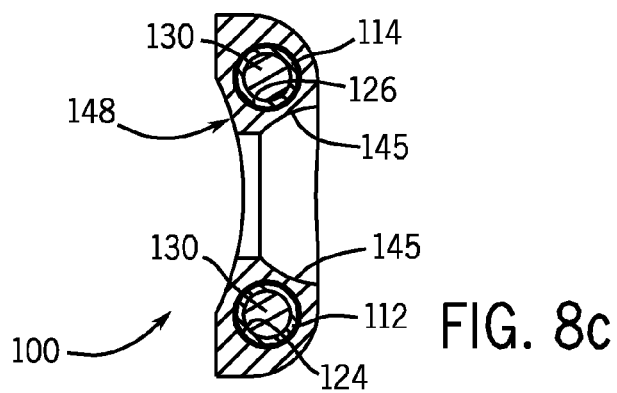

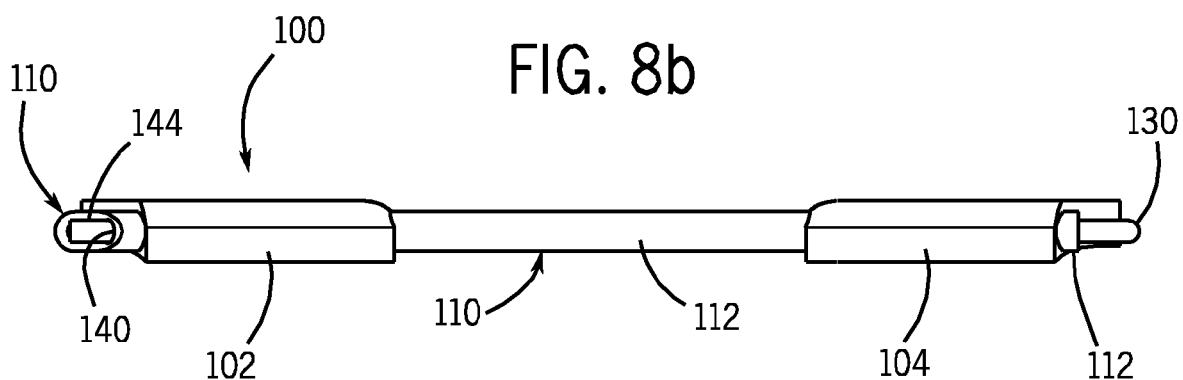
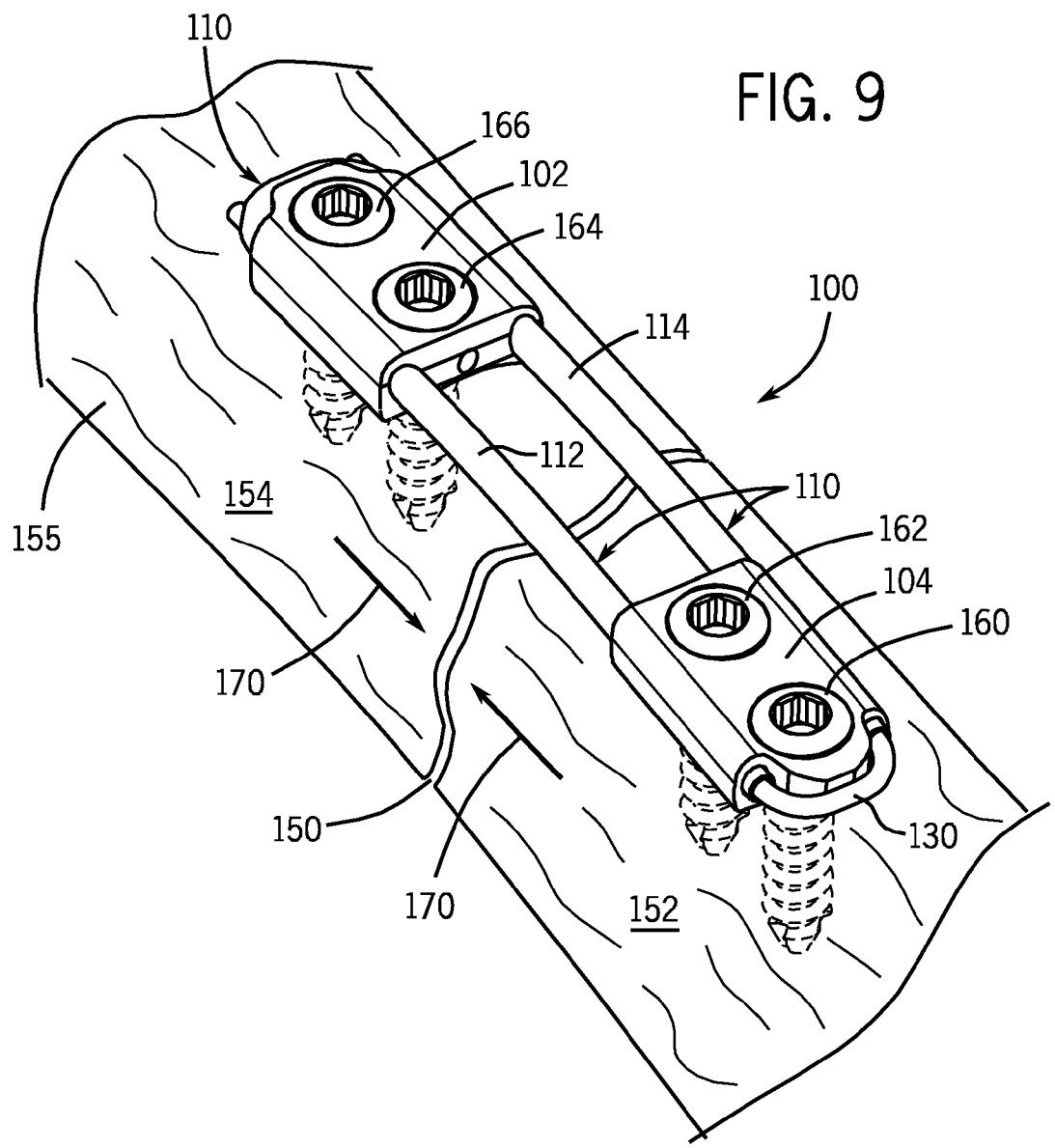

BONE BRIDGE PROVIDING DYNAMIC COMPRESSION ON BONE FRACTURES

CROSS REFERENCE TO RELATED APPLICATIONS

This application claims the benefit of U.S. patent application Ser. No. 11/454,344 filed on Jun. 16, 2006, which is incorporated herein by reference.

BACKGROUND OF THE INVENTION

1. Field of the Invention

This invention relates generally to medical and surgical devices and methods and more specifically to orthopedic bone plates and bone staples suitable for internally fixating and stabilizing fractured bones.

2. Description of the Related Art

Many bony fractures require stabilization that cannot be provided by external splints or casts; internal fixation is therefore required. Bone plates and bone staples are among the most common artificial orthopedic implants, and are commonly used to stabilize and internally fixate bony fractures.

A conventional bone plate is essentially a rigid metal plate drilled with guide holes through which bone screws can be passed. Bone screws are usually inserted through the mounting holes and threaded into the bone above and below the fracture to fix the bone plate, thereby rigidly stabilizing and fixating the fracture. Often the bone plate is removed after healing has occurred (although not necessarily). A conventional bone staple is generally a simple device comprising a crossbar and two spaced apart legs or arms extending down on opposite ends of the crossbar. The arms are introduced into the bone on opposite sides of a bone fracture to hold the staple in place and help stabilize a small bone fracture.

More recently, physicians have given increasing emphasis on bone plates, staples and like devices which are capable of providing compression of the fracture as well as stabilization. However, most conventional compression plates and staples are made of metal materials having moduli of elasticity much higher than that of bone and therefore a limited ability to apply controlled amounts of compressive force to a fracture.

In particular, use of such bone plates produces a mechanical system in which the majority of the stress is borne by the plate rather than the bone, a situation sometime referred to as "stress-shielding." This situation is deleterious even to healthy, uncompromised bone, and can seriously impair the healing process in a fractured bone. Furthermore, it is now known that a controlled compressive load should be maintained across a fracture to promote rapid healing. Conventional, static bone plates do not provide or maintain such conditions.

Some bone plates and staples include provision for introducing compression across a bone fracture. In the case of bone plates the most common methods of producing compression rely on unusual bone screws or an unusual relationship between the screw and the mounting holes. In the case of bone staples the crossbar may be designed to pull the arms inward after the staple is surgically installed and thereby provide a limited amount of compressive force across the fracture. Such methods can introduce initial compression, but the compression is difficult to maintain. Small movements of the bone can interact with the typically high-modulus metallic plate or staple, causing large fluctuations of the compressive load. Furthermore, some resorption may occur as a prelude to osteosynthetic growth, resulting in contraction of the bone in the region of the fracture and releasing the compressive force. Even small contractions will produce slack sufficient to leave the fracture without compression (because the high-modulus metal plate cannot accommodate the contraction).

Alternatives to metal materials have been explored by some, including bioabsorbable materials and synthetic composite materials. Such materials appear promising, but offer their own challenges. There are still unanswered questions concerning the biocompatibility, strength, stability, reliability, wear, and ease of manufacture and handling. Most physicians continue to prefer metal plates to structures using synthetic materials for these reasons.

SUMMARY OF THE INVENTION

In view of the above problems, the present invention is an orthopedic bone plate system or bone bridge, suitable for internally fixating and stabilizing fractured bones, comprising: an elongated structure, capable of contraction in a longitudinal direction and having at least two ends, the structure further having at least two fixation points adapted to be fixated to a fractured bone with the fixation points on opposing sides of a fracture. An elastic, polymer cable or microcable is longitudinally stretched and coupled in tension to the elongated structure between the points of fixation, capable of causing the structure to contract in the longitudinal direction. The significant relationship is that at least two points of fixation are provided across the bone fracture with those points being capable of elastically loaded displacement in relation to each other in a longitudinal direction so as to result in a controlled compressive force being applied to the fracture.

More specifically, a bone bridge in accordance with the present invention comprises a first bone fragment plate intended to be secured to a first bone fragment by one or more bone screws or the like and a second bone fragment plate intended to be secured a second bone fragment by one or more bone screws or the like. The bone bridge also includes a U-shaped hollow tube having a reverse bend and two elongate parallel hollow legs that are open at their ends opposite from the bend. The legs of the tube extend through channels or passages in the bone fragment plates allowing the plates to slide along the legs with the first plate at one end toward the bend in the tube and the second plate at the opposite end toward the open ends of the legs. An elastic microcable extends fully down the legs and across from one leg to another at their open ends. The ends of the microcable are secured in place at the end of the U-shaped tube near the bend. In use the first bone fragment plate is retained in position at one end of the bone bridge by the bend in the U-shaped tube while the second one bone fragment plate is movable and engages the elastic microcable which wraps around its outer end. The elastic microcable is maintained in tension pulling the bone fragment plates toward each other and accordingly the bone bridge applies a controlled compressive force to a bone fracture.

These and other features and various advantages of the invention will be apparent to those skilled in the art from the following detailed description of preferred embodiments, taken together with the accompanying drawings, in which:

BRIEF DESCRIPTION OF THE DRAWINGS

FIG. 1 is an elevated perspective view of a first embodiment of the bone bridge apparatus of the present invention;

FIGS. 2a, 2b, 2c and 2d are a plan view from above, plan view from below, a side view and a cross-sectional view, respectively, of the apparatus of FIG. 1 (2d being cross-sectional along lines 2d-2d in FIG. 2a) in accordance with the present invention;

FIG. 7 is an elevated perspective view of a second embodiment of a bone bridge apparatus in accordance with the present invention;

FIGS. 8a, 8b and 8c are a plan view, a side view and a cross-sectional view, respectively, of the apparatus of FIG. 7 (8c being cross-sectional along lines 8c-8c in FIG. 8a) in accordance with the present invention; and FIG. 9 is an elevated perspective view of the apparatus of FIG. 7 surgically installed across a bone fracture and in operation in accordance with the present invention.

DETAILED DESCRIPTION OF THE INVENTION

Figure 2B:
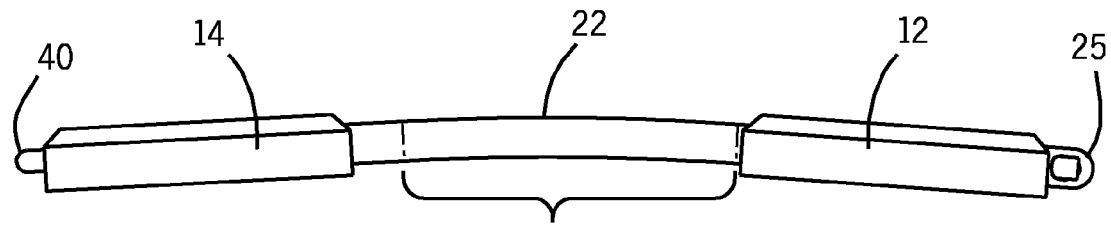

FIG. 1 shows generally a particular first embodiment of a bone plate system or bone bridge 10 in accordance with the invention. The bone bridge 10 is shown in a relaxed state as further explained below. The bone bridge 10 includes a first fixed bone fragment plate 12 and a second movable bone fragment plate 14 each of which has a countersunk hole or aperture 16 and 18 through which bone screws or other fasteners may extend to individually fix the plates 12 and 14 to different bone fragments on different sides of a bone fracture. A hollow U-shaped cylindrical tube 20 has a 180 degree reverse bend 25 at its proximal end and defines two parallel spaced-apart legs 22 and 24 open at their distal ends. The plates 12 and 14 and the U-shaped tube 20 are preferably fabricated from stainless steel or titanium. The legs 22 and 24 extend through the plates 12 and 14 in cylindrical channels or passages 30 and 32 in plate 12 and cylindrical channels or passages 34 and 36 in plate 14. The passages 30, 32, 34 and 36 are of a somewhat larger inside diameter than the outside diameter of the legs 12 and 14 and therefore the plates 12 and 14 are free to slide up and down along the legs 12 and 14 of the tube 20, subject to retention at the far ends of the tube as further described below. An elastic polymer cable or microcable 40 extends around the outer end 42 of the plate 14 down through both of the hollow legs 12 and 14 from the distal end (open end) of the U-shaped tube 20 to the proximal end of the tube 20 (closed end, at the bend 25) toward the outer end 44 of the plate 12 (as the plate 12 rests in bend 25). The elastic polymer microcable 40 preferably comprises a relatively lower strength, elastic polymer core, such as nylon, clad in a relatively stronger woven jacket, said woven jacket including ultra-high molecular weight polyethylene fibers. The ends of the elastic microcable 40 are secured within the tube 20 by being crimped in place in proximity to the proximal end of the tube 20 at the working position of the fixed plate 12 which effectively serves to connect the ends of the microcable 40 to the plate 12 during operation of the bone bridge. In use the microcable 40 stretches allowing the movable plate 14 to slide along the legs 12 and 14 both toward and away from the fixed plate 12 under controlled tension provided by the elastic microcable 40 which continuously engages the movable plate 14. The tensile force provided by the elastic microcable 40 is applied as a compressive force on a bone fracture that promotes healing when the bone plates 12 and 14 are secured to bone fragments and deployed across the bone fracture and the plates 12 and 14 are suitably spaced apart (properly beyond their relaxed position). A spacer (not shown in FIG. 1) may be coupled between the plates 12 and 14 and used to maintain the bone bridge 10 in a tensioned pre-delivery state with the plates properly spaced apart prior to and during the process of surgical installation. After surgical installation the spacer is removed and the bone bridge is placed in a released state. In this state the tension provided by the microcable 40 is transferred to the plates 12 and 14 which are urged toward one another. A compressive force is thereby applied to the bone fragments on which the plates 12 and 14 are attached and applied along the fracture between them. The compressive force promotes proper healing of the fracture. It should be understood that the bone bridge 10 shown in FIG. 1 (and FIGS. 2a-2d) is in a relaxed state meaning that the microcable 40 is not under tension and the bone fragment plates 12 and 14 are not appropriately separated for surgical installation and use. Prior to or during surgical installation the bone fragment plates 12 and 14 would normally be spaced apart and held or locked in this position by a simple spacer situated between the plates or by a special delivery tool adapted for holding and positioning the bone bridge 10 with the microcable 40 maintained in a controlled degree of tension calculated upon release to provide the required compressive force onto a fracture. Optionally, the apparatus could be prepackaged with the spacer installed and preloaded with tension. After installation the spacer is then removed or the tool disengaged to allow the bone bridge 10 to deliver a desired compressive force across the target fracture.

The elastic microcable 40 is characterized by a force function capable of storing significant energy as it is stretched. The cable thereby provides a controlled compressive force over the expected operational range of motion for a fracture. The microcable 40 is deployed along most of its length within the tube 20 which protects and supports the cable while enabling a compact design. An exemplary bone bridge 10 might use a 0.032 inch (0.8 mm) diameter microcable 40 providing on average 100 Newtons of compressive force across a fracture falling off from about 150 Newtons of force at maximum extension. Such a bone bridge device would be about 28.8 mm long, 7.6 mm wide and 1.9 mm thick. Each of its bone fragment plates 12 and 14 would be about 8.9 mm long and be adapted to mount 2.5 mm bone screws with hemispherical heads allowing the screws to be mounted at an angle if necessary. The plates would be mounted and slidable on 1.5 mm diameter legs 22 and 24 defined by as a part of U-shaped tube 20. However, bone bridges may be of different sizes for use on fractures of different dimensions and in different types of bones. The dimensions of the bone bridge 10 are required be sufficient to accommodate the desired contraction and/or expansion of the device and deliver the desired compressive force on the fracture during healing and withstand the operative forces associated with the bone and body position involved. For example, in one embodiment, enough length should be provided to permit 1 to 5 millimeters of contraction or expansion between the bone fragment plates.

Figure 2C:
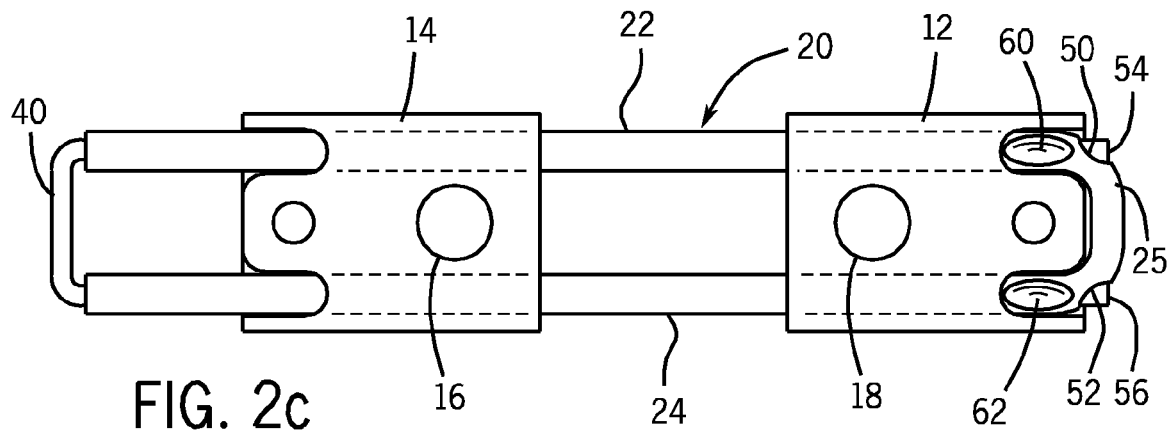

FIGS. 2a-2d show different views and aspects of the bone plate system or bone bridge 10 in accordance with the invention, again in a relaxed state. In particular FIGS. 2a, 2b and 2c illustrate how the tube 20 wraps around the outer end 44 of the fixed plate 12 at its bend 25 while the microcable 40 correspondingly wraps around the outer end 42 of the movable plate 14. The bone fragment plates 12 and 14 are slidably engaged on the legs 22 and 24 allowing the plates a single degree of freedom for longitudinal displacement. The movement of the plate 12 is limited by the bend 25 at the proximal end of the tube 20 while the movement of the plate 14 is limited by the microcable 20 at the distal end the tube 20. The apertures 16 and 18 are centrally positioned on the plates 12 and 14 to allow bone screws or the like to be properly secured through the apertures into bone fragments in order to affix the plates 12 and 14 to different bone fragments spanning a bone fracture. FIGS. 2a and 2b also show holes 50 and 52 in the tube 20 at transversely opposite sides of the bend 25 in direct alignment with the legs 22 and 24. The holes 50 and 52 allow the ends 54 and 56 of the microcable 40 to extend out of the proximal end of the tube 20 during assembly so that the full passage of the microcable down the legs 22 and 24 can be visually confirmed prior to the microcable ends being crimped in place and their far ends being conveniently trimmed off. In particular, FIG. 2b shows the crimping points 60 and 62 where the tube 20 is folded upon itself into a crimped shape for squeezing and securely retaining the microcable 40 in (operational) proximity to the fixed plate 12. FIG. 2c illustrates how the bone bridge 10 and more specifically the legs 12 and are slightly curved, and how the bone bridge assumes a downward facing (toward the bone and fracture) concave shape 70 along its longitudinal axis. This concave shape 70 provides the bone bridge 10 with pre-stressed configuration that compensates for the strain and deformation resulting from compressive forces in use and helps assure that uniform pressure is applied across the fracture to which the bone bridge is applied. FIG. 2d shows the legs 22 and 24 of the tube 20 running in the passages 34 and 36 with sufficient clearance to enable an easy sliding engagement between the plate 14 and legs 22 and 24 and depicts the countersink 66 of one of the apertures 18 designed to accommodate the hemispherical head of a bone screw.

The stabilizing structure comprising the bone bridge 10 provides structural stability in at least two degrees of freedom: specifically, the structure is substantially rigid with respect to bending moment and torque about the longitudinal axis of the structure. These qualities permit the structure to splint a fracture much like a conventional bone plate. However, unlike conventional bone plates, the bone bridge of the present invention is capable of substantial contraction (or in some embodiments, expansion) in the longitudinal direction.

Figure 3:
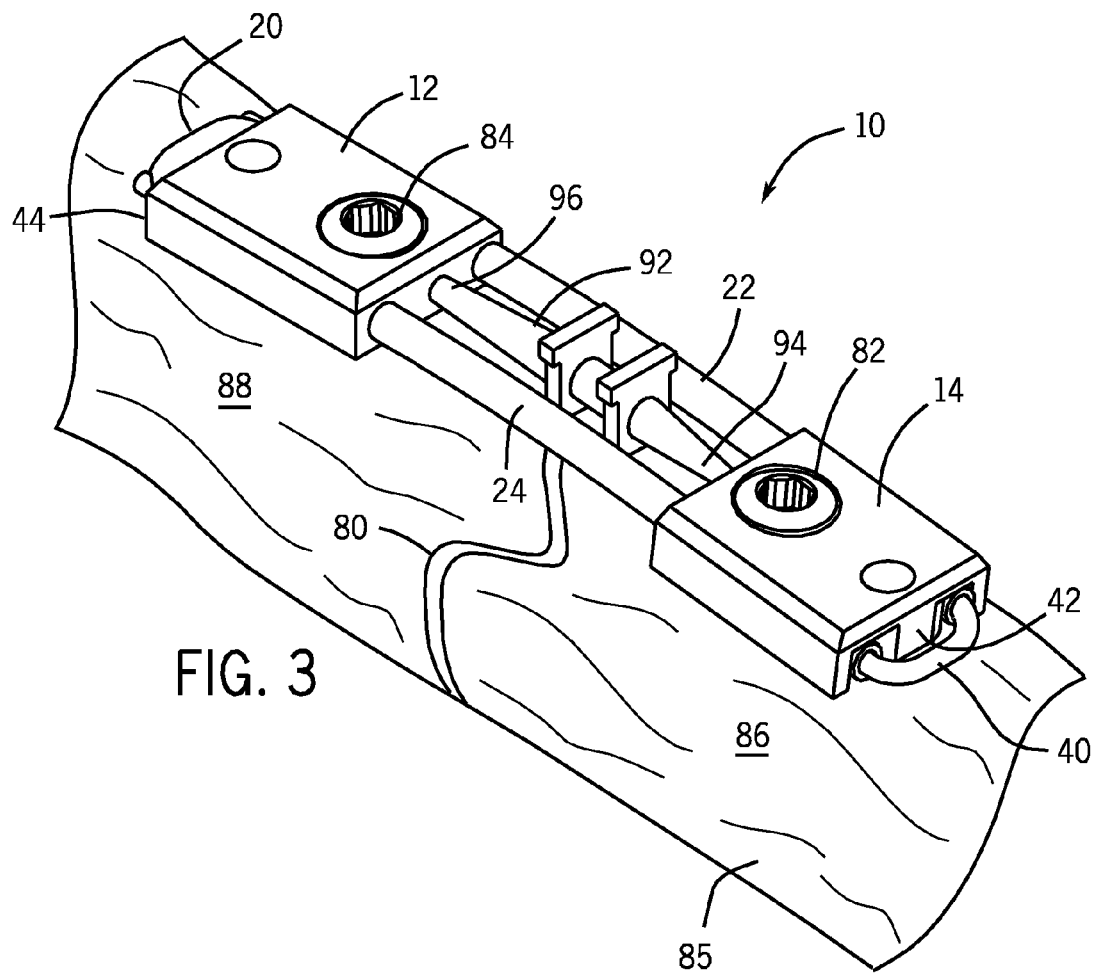
FIG. 3 is an elevated perspective view of the apparatus of FIGS. 1 and 2a-d surgically installed across a bone fracture but with a spacer between the plates and the device in a pre-delivery condition and not yet released for operative use in accordance with the present invention.
Figure 4:
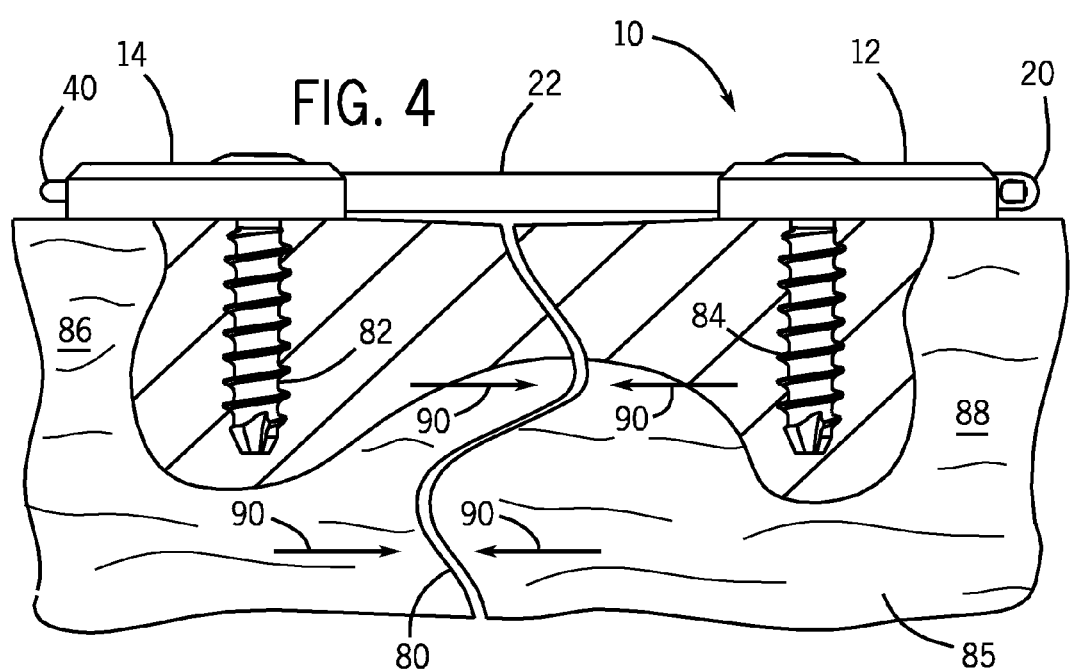
FIG. 4 is a side view of the apparatus of FIGS. 1, 2a-d and 3 surgically installed across a bone fracture and in operative use in accordance with the present invention.

FIGS. 3 and 4 show the bone plate system or bone bridge 10 in accordance with the invention surgically installed on a long bone 85 across a bone fracture 80. The bone bridge 10 is in a tensioned (pre-delivery) state following the plates 12 and 14 being spaced apart at a fixed distance to provide a controlled amount of compression and held in position during surgical installation in anticipation of being released to allow the compressive force to be applied to a fracture. The bone screw 82 is installed to anchor the movable plate 14 onto the bone fragment 86 and the bone screw 84 is installed to anchor the movable plate 14 onto the bone fragment 88. The microcable 40 is engaged with and around the movable plate 14 while the tube 20 is engaged with and around the fixed plate 12. The plates 12 and 14 are spaced apart along the legs 12 and 14 with the microcable 40 in tension pulling the plates toward each other and correspondingly furnishing the compressive force illustrated by arrows 90 on the fracture 80. In particular FIG. 3 shows the bone bridge 10 with the elongate pre-delivery spacer 92 in place centrally positioned and separating the plates 12 and 14 and accordingly absorbing the compressive force generated by the elastic microcable 40. FIG. 4 shows the bone bridge 10 with the spacer 92 extracted and the bone bridge in medical operation. The elastic cable 40 is in tension and acts to urge the plates 12 and 14 toward one another on the legs 12 and 14 along the longitudinal axis of the bone bridge and the fractured bone. The bone screws 82 and 84 transfer this force to the bone fragments 86 and 88 and a compressive force is correspondingly applied to the fracture 80. It should be noted that in operation with the microcable in tension and the fracture under compression the bone bridge 10 lays flat along the surface of the bone 85.

As reference above some embodiments the bone bridge 10 of the invention also include a spacer, such as the elongate rigid spacer 92 as shown in FIG. 3, that acts as a locking mechanism for locking the bone plates in a pre-tensioned, extended pre-delivery position. The spacer 92 extends between the plates 12 and 14 and may have its pointed ends 94 and 96 engaged in shallow indents on the inner surfaces of the plates for helping to retain the spacer in position. In the locked position the fixation points established by the plates 12 and 14 are maintained in an extended, pre-tensioned position before and during fixation to the fractured bone. After fixation to the bone with the plates disposed on opposing sides of the fracture, the spacer 92 is released and extracted, causing the pre-set tension to be transferred to the bone, tending to compress the fracture by a pre-determined force linearly increasing with separation of the bone plates but controlled to only change by limited amounts over the operative range of motion of the apparatus, as hereinafter described in greater detail with respect to the graph provided in FIG. 5. The bone and bone plate thus become a mechanical system in equilibrium: in the longitudinal direction the bone fragment plates, under tension from the elastomeric cable, tension is supplied which is countered by equal longitudinal compression of the bone across the fracture. Though capable of contraction in the longitudinal dimension, the bone plate is generally rigid in transverse, shear, and torque directions to stabilize and splint the fracture during healing.

A microcable suitable for use as elastomeric cable 40 in the invention should have at least two qualities: a) relatively high breaking strength, in the range at least 150 Newtons and preferably 300 Newtons for a cable of 0.5-0.8 mm in diameter, and b) the ability to maintain the tension within a desired range notwithstanding substantial displacement (plus or minus) of the fracture. It is known that fractures may slightly contract due to resorption prior to healing, which may create shortening of the bone of up to a few millimeters. It is also known that living bone under changing loads flexes, extending and contracting in response to load during normal activity. For this reason, to maintain proper compression on the fracture the cable in the invention should preferably possess specific force/extension characteristics at the working tension (in the 20-300 Newton range) although this depends on the dimensions of the bone bridge device itself. We can define an axial modulus parameter Q as the cable tension (in Newtons) multiplied by the cable's static (unloaded) length, divided by the quantity working length minus unloaded length. For preferred embodiment, this axial modulus Q should preferably be below 1400 (Newtons), and more preferably in the Range of 160 to 1800 Newtons. Higher values impose difficulties in accurately imposing and maintaining tension, based on the precision of the assumed cable take-up mechanism. In other words, Q values below 1800 are preferred so that the working elongation is a manageable displacement at the working tension.

The cable's force/extension characteristic should preferably be both strong and capable of significant elongation in the working region. Weaker elastomeric cables (such as urethane monofilament) are capable of significant contraction/extension while maintaining substantially constant tension; but such cables are not suitable because they exert insufficient working tension. On the other hand, metal alloy cables exert significant tension but do not maintain the working tension within a zone of tolerance if stretched or slackened by the degree of movement normally associated with most fractures. Metal cables cannot stretch over the load ranges required, primarily because of their high elastic modulus.

The strength and extension characteristics discussed above should also be understood in the context of working lengths and diameters suitable for use in a bone bridge apparatus. Suitable cable diameters for this application would be in the 0.5-2.0 millimeter range; working lengths are typically in the 5-30 cm range, constrained by the length of the bone plate apparatus.

Suitable cable preferably should also allow substantial elongation without danger of failure. For this reason the cable should preferably be capable of extension by a substantial percentage, preferably 50 and more preferably at least 100 percent, without significant risk of failure. Furthermore, it will be apparent that bio-compatible materials should be employed, more specifically, bio-compatible materials that can be suitably sterilized and preferably packaged in hermetically sealed packaging for distribution.

The inventors have found that a preferred cable can be engineered as a relatively lower strength, monofilament polymer core (for example, nylon, silicone or urethane core) surrounded by a woven, relatively higher strength polymer jacket woven from ultra-high molecular weight polyethylene fibers. The jacket fibers significantly increase the strength, reliability, and maximum extension before failure of the cable.

A method of fixing a fracture in accordance with the invention can be visualized by reference to FIG. 4 showing the bone bridge 10 in relation to a long bone 85, with a fracture at 80. We assume that the bone bridge 10 is pre-tensioned and locked (either at the manufacturer, prior to packaging, or by the surgeon in the operating room); otherwise, the device should be pre-tensioned and locked as a preliminary step. To internally fix the fracture, the fracture is first reduced (typically during open surgery). The surgeon then places the bone bridge 10 adjacent to the bone 85, across the fracture 80 in a splint-like configuration, with the longitudinal axis (defined by the bone and fracture and the permitted direction of contraction of the bone bridge) across the fracture 80.

Once positioned, the bone bridge 10 is secured to the bone 85 by fixing the opposing bone fragment plates 12 and 14 to the bone fragments 86 and 88 on opposite sides of the fracture 80. Optionally, a further bone bridge (or multiple devices) may be positioned to further support and stabilize the fracture. As previously discussed, the plates 12 and 14 may be fixed, for example, by placement of conventional bone screws passed through the fixation holes 16 and 18. After the bone fragment plates 12 and 14 are fixed on opposite sides of the fracture 80, the bone bridge 10 can be unlocked into a released state with the microcable 40 tensioned. Thereupon, there is no obstacle (other than the bone) to contraction of the slidable members toward one another. Consequently, the bone plate tends to contract under the tension of the cable 40, drawing the plates 12 and 14 toward one another and compressing the fracture by a predetermined and controlled load.

Figure 5:
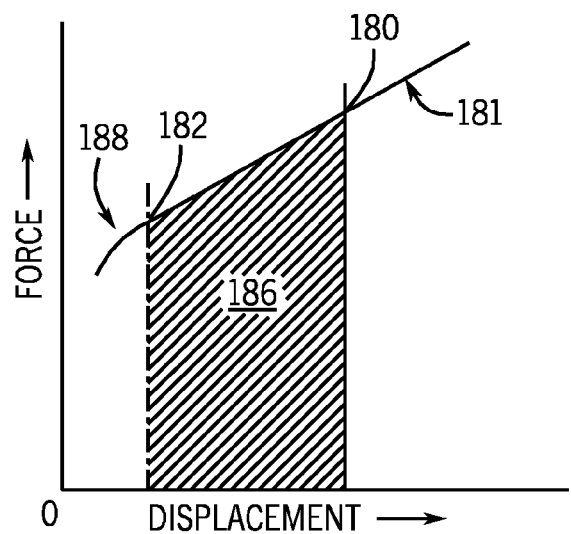
FIG. 5 is a graph of force as a function of extension for a bone bridge in accordance with the invention, illustrating elastic and energy storage characteristics.

The graph of FIG. 5 illustrates force vs. displacement and energy storage in the apparatus of the invention. The force as a function of displacement is substantially linear with a limited rate of change (slope) in a significant region of the graph. In preferred embodiment, the invention is pre-tensioned or biased at a point 180 on curve 181, calculated to enable operation in a substantially linear region from points 180-182 of the curve 181. The bias point 180 is predetermined to allow room for contraction and/or expansion without either a) breaking the cable, or b) incurring excessively low or excessively high tension. The bias point of the cable in the invention departs from prior bone plates, which have useful active ranges of only tenths of a millimeter due to the extremely high modulus of the solid metal parts as previously used.

The graph of FIG. 5 also illustrates energy storage in the apparatus of the invention, which is an alternate way of viewing or describing the action of the apparatus. The total area under the curve 181 represents the energy stored in the apparatus of the invention (almost entirely in the elastomeric cable) with the tension set at the predetermined bias point. The apparatus can contract to the limit 182, performing work equal to the hatched area 186 (part of the total area under 181).

In a typical embodiment the bias point is set at a point such that the pre-loaded apparatus stores energy of at least 0.1 Joules. More preferably, the preloaded apparatus stores energy of at least 0.5 Joules, and more specifically in the range 0.5 to 10 Joules. This energy storage is believed to provide significant advantage over the relatively low energy storage of prior devices. FIG. 5 also shows that the elastic curve of the device has a corner, and rolls off rapidly at lower extensions (region 188). The energy storage capacity of the invention provides advantage in at least two ways: the bone plate better accommodates contraction and expansion during healing, and the tension provides a dynamic load on the bone during healing, thereby preventing "stress shielding" and the resulting atrophy of bone which can occur with static metal bone plates.

Figure 6:
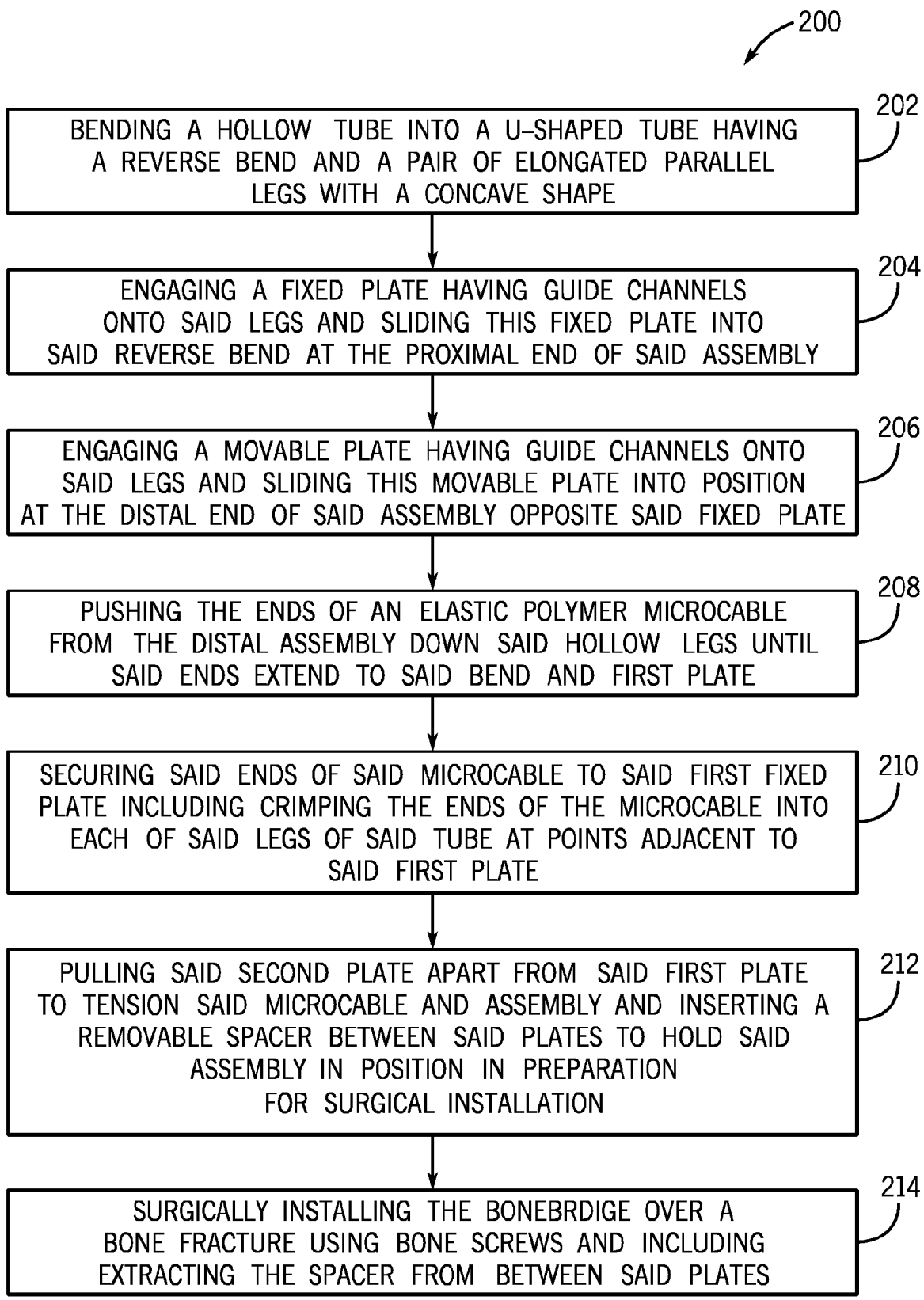
FIG. 6 is a flowchart illustrating the process steps associated with the manufacture and assembly of a bone bridge apparatus in accordance with the present invention.

FIG. 6 Shows a process 200 of assembling a bone bridge 10 including the process steps 202, 204, 206, 208, 210, 212 and 214. In accordance with step 202 the process 200 starts with a standard stainless steel tube that is placed in a jig and bent into a U-shape with a reverse (180 degree) bend and a pair of elongate spaced apart parallel legs that preferably have a slightly concave configuration along their longitudinal axis. In step 204 a first bone fragment plate is having channels mating with the legs is slid onto the legs until it reaches the far proximal end of the tube at its bend where it is (operationally) fixed in place. In step 206 another second bone fragment plate having channels mating with the legs is slid onto the legs and positioned at the distal end of the tube so as to be free to slide and remain longitudinally movable. Thereafter, pursuant to step 208, a suitable length of elastomeric polymer microcable selected to provide a controlled tensile force is pushed down the tube from both its open ends until the microcable extends out from holes drilled in the tube at its far proximal end at the bend thereby also forming a loop around the second plate. In step 210 the legs of the tube are crimped securing the ends of the microcable in place in proximity to the bend in the tube and thereby effectively securing the microcable to the first bone fragment plate. In step 212, in preparation for surgical installation, the bone fragment plates are pulled apart to provide a controlled amount of compressive force and a spacer is inserted between the plates to maintain them in a spaced apart position. Thereafter, in the final step 214, the bone bridge is surgically installed by attaching the first and second plates to opposing bone fragments bridging the bone fracture under treatment and the spacer is extracted to apply the controlled compressive force to and across the bone fracture.

FIG. 7 shows generally a particular second embodiment of a bone plate system or bone bridge 100 in accordance with the invention in a relaxed state. The embodiment includes a first fixed bone plate 102 and second movable bone plate 104 each of which has one or more countersunk holes or apertures 106 and 108 through which bone screws or other fasteners may extend to individually fix the plates 102 and 104 to different bone fragments on different sides of a bone fracture. A hollow U-shaped cylindrical tube 110 has a 180 degree reverse bend 115 at its proximal end and defines two parallel spaced-apart legs 112 and 114 open at their distal ends. The plates 102 and 104 and the U-shaped tube 110 are preferably fabricated from stainless steel. The legs 112 and 114 extend through the plates 102 and 104 in cylindrical channels or passages 120 and 122 in plate 102 and cylindrical passages 124 and 126 in plate 104. The passages 120, 122, 124 and 126 are of a slightly larger inside diameter than the outside diameter of the legs 112 and 114 and therefore the plates 102 and 104 are free to slide up and down along the legs 112 and 114 of the tube 110, subject to retention at the far ends of the tube 110 as described below. An elastic polymer cable or microcable 130 extends around the curved outer end 132 of the plate 104 transits down the interior of the legs 112 and 114 from the proximal end (open end) of the U-shaped tube 110 to the distal end of the tube 110 (closed end, at the bend 115) at the curved outer end 134 of the plate 102. The elastic polymer microcable 130 preferably comprises a relatively lower strength, elastic polymer core, such as nylon, clad in a relatively stronger woven jacket, said woven jacket including ultra-high molecular weight polyethylene fibers. The ends of the elastic microcable 130 are secured within the tube 110 by being crimped in place in proximity to the proximal end of the tube 110 at the working position of the fixed plate 102 (the ends of the microcable 130 are operationally affixed to the plate 102). In use the microcable 130 stretches allowing the movable plate 104 to slide along the legs 112 and 114 toward and away from the fixed plate 102 under controlled tension provided by the elastic microcable 130 which continuously engages the movable plate 104 during use. When the bone plates 102 and 104 are secured to bone fragments and deployed across a bone fracture and the plates 102 and 104 are suitably spaced apart the tensile force provided by the elastic microcable 130 is applied as a compressive force on a bone fracture that promotes healing. FIGS. 8a-8c generally show different views of the bone plate system or bone bridge 100 in accordance with the invention, again in a relaxed state. FIGS. 8a and 8b illustrate how the U-shaped tube 110 wraps around the curved outer end 134 of the fixed plate 102 at its bend 115 while the microcable 130 correspondingly wraps around the curved outer end 132 of the movable plate 104. The legs 112 and 114 of the U-shaped tube 110 run through the matching passages 120 and 122, and 124 and 126 that are disposed on opposite transverse sides of the plates 102 and 104 slidably engaging the plates on the legs of the tube 110. The apertures 106 and 108 are centrally positioned on the plates 102 and 104 to allow bone screws or the like to be secured through the apertures into bone fragments in order to affix the plates 102 and 104 to opposing bone fragments spanning a bone fracture. FIGS. 8a and 8b also show holes 140 and 142 in the tube 110 on opposite sides of the bend 115 in line with the legs 112 and 114. The holes 140 and 142 allow the ends 144 and 146 of the microcable 130 to extend out of the proximal end of the tube 110 during assembly so that the full passage of the microcable down the legs 112 and 114 can be visually confirmed prior to their being crimped in place and the cable ends can be conveniently trimmed off. FIG. 8c shows the legs 112 and 114 of the tube passing through the passages 124 and 126 in the plate 104, depicts the countersink 145 of one of the apertures 108 and illustrates the transverse concave configuration 148 of the bone bridge which allows for easier centering on generally convex bone surfaces.

FIG. 9 shows the second embodiment of a bone plate system or bone bridge 100 in accordance with the invention surgically installed on a bone 155 and across a bone fracture 150. The bone bridge 100 is in a tensioned state following the plates 102 and 104 being spaced apart at a fixed distance to provide a controlled amount of compression, held in position during surgical installation and subsequently released to allow a compressive force to be applied to a fracture. The bone screws 160 and 162 are installed to anchor the movable plate 104 onto the bone fragment 152. The bone screws 164 and 166 are installed to anchor the fixed plate 102 onto the opposing bone fragment 154. The microcable 130 is engaged with and around the movable plate 104 while the tube 110 is engaged with and around the fixed plate 102. The plates 102 and 104 are longitudinally spaced apart along the legs 112 and 114 with the microcable 130 in tension pulling the plates toward each other and correspondingly furnishing the compressive force illustrated by arrows 170 on the fracture 150.

While several illustrative embodiments of the invention have been shown and described, numerous variations and alternate embodiments will occur to those skilled in the art. One of the slidable members 10 or 12 could be integrated with the rail 14, allowing the second member to slide for contraction. Variants of the rail could be used, including telescoping rails, multiple rails, tongue and groove slots, dovetailed slots and tongue, or other telescoping or contractible mechanisms. The U-shaped tube 110 could have a different cross section such as being square or hexagonal. A single tube 110 could be employed in a manner similar to a rail with the microcable running down the tube but connected at opposite ends to opposing plates. Various types of holes and bone screws could be used, including slanted screws, oval holes, slots, and interfering arrangements of screws and slot as known in the art. The slidable members and/or rail could be contoured in cross section, and the contact points between the members and the bone could be varied. For example, minimal contact feet could be employed, or aggressive features such as teeth could be provided to grip the bone. Such variations and alternate embodiments are contemplated, and can be made without departing from the spirit and scope of the invention as defined in the appended claims.

We claim:

1. A bone bridge for use in stabilizing a bone fracture, comprising:
   a) a pair of longitudinally parallel and transversely spaced-apart elongate hollow cylindrical tubes having an inner diameter and an outer diameter;
   b) a first plate fixedly secured toward proximal ends of said tubes and having one or more mounting apertures for receiving one or more fasteners for attaching said first plate to a first bone fragment, wherein said hollow tubes are defined by a single U-shaped cylindrical tube which also extends around said first plate;
   c) a second moveable plate, slidably mounted on said tubes toward their distal ends and having one or more mounting apertures for receiving one or more fasteners for attaching said second plate to a second bone fragment; and
   d) an elastic polymer cable secured to said first plate and running in a U-shaped configuration through said tubes and around said second plate in a state of controlled tension so as to provide a compressive force on said bone fracture.

2. A bone bridge for use in stabilizing a bone fracture, comprising:
   a) an U-shaped hollow tube including a direction reversing bend and a pair of longitudinally parallel and transversely spaced-apart elongate legs having an inner diameter and an outer diameter;
   b) a first plate fixedly secured to the proximal end of said U-shaped tube at said bend and having one or more countersunk mounting apertures for receiving one or more bone screws for use in attaching said first plate to a first bone fragment;
   c) a second moveable plate mounted on said tube toward its distal end opposite said first plate so as to be able to longitudinally slide along said legs and having one or more countersunk mounting apertures for receiving one or more bone screws for attaching said second plate to a second bone fragment; and
   d) an elastic polymer cable secured to said first plate and running in a U-shaped configuration through said tube and around said second plate in a state of controlled tension so as to provide a compressive force on said bone fracture.

3. The bone bridge of claim 2, wherein:
   said elastic polymer cable comprises a relatively lower strength, elastic polymer core clad in a relatively stronger woven jacket, said woven jacket including ultra-high molecular weight polyethylene fibers.

4. The bone bridge of claim 2, wherein:
   said U-shaped tube includes a pair of holes at its proximal end from which the ends of said cable can extend so that the cable can be dimensioned and trimmed during manufacture, and said cable is secured to said first plate by being crimped into said tube at points adjacent to said bend and first plate.

5. The bone bridge of claim 2, wherein:
   said legs are slightly curved to articulate said bone bridge into a slightly concave shape facing toward said bone fracture so as to apply approximately equal compressive force across said bone fracture when said bone bridge is in use.

6. The bone bridge of claim 2, further including:
   a removable spacer for separating and holding said first and second plates apart as the bone bridge is being surgically installed.

7. A bone bridge for use in stabilizing a bone fracture between two bone fragments, comprising:
   a) a first bone fragment plate having one or more mounting apertures for receiving one or more fasteners for attaching said first plate to a first bone fragment;
   b) a second bone fragment plate having one or more mounting apertures for receiving one or more fasteners for attaching said second plate to a second bone fragment;
   c) a guide structure for limiting the motion between said first and second bone plates to movement along a longitudinal axis defined by said bone fragments and for linearly guiding the movement of said first bone plate with respect to said second bone plate, wherein said guide structure for limiting the motion between said first and second bone plates comprises a U-shaped hollow tube having a bend which extends around and operationally secures said first plate and having a pair of parallel hollow legs on which said second plate is slidably mounted,
   d) an elastic polymer cable coupled to said first and second bone plates for generating a tensile force between said first and second bone plates along the longitudinal axis defined by said bone fragments in order to provide a compressive force between said bone fragments; and
   e) a removable elongate spacer extending between said first and second plates for use in holding said plates in a spaced apart configuration with said elastic polymer cable in tension during surgical installation of the bone bridge.

* * * * *